US012692549B2

(12) United States Patent
Aparicio et al.

(10) Patent No.: US 12,692,549 B2
(45) Date of Patent: Jul. 28, 2026

(54) IN VITRO METHOD FOR THE PROGNOSIS OF PATIENTS SUFFERING FROM HER2-POSITIVE BREAST CANCER

(71) Applicants: Hospital Clinic De Barcelona, Barcelona (ES); Fundació De Recerca Clinic Barcelona-Institut D'Investigacions Biomèdiques August Pi I Sunyer, Barcelona (ES); Asociación Solti, Barcelona (ES); Universitat De Barcelona, Barcelona (ES); Università Degli Studi Di Padova, Padua (IT)

(72) Inventors: Aleix Prat Aparicio, Barcelona (ES); Laia Paré Brunet, Barcelona (ES); Pierfranco Conte, Pisa (IT); Maria Vittoria Dieci, Padua (IT); Valentina Guarneri, Padua (IT)

( * ) Notice: Subject to any disclaimer, the term of this patent is extended or adjusted under 35 U.S.C. 154(b) by 660 days.

(21) Appl. No.: 18/018,295

(22) PCT Filed: Jul. 26, 2021

(86) PCT No.: PCT/EP2021/070788
§ 371 (c)(1),
(2) Date: Jan. 27, 2023

(87) PCT Pub. No.: WO2022/023235
PCT Pub. Date: Feb. 3, 2022

(65) Prior Publication Data
US 2024/0084390 A1     Mar. 14, 2024

(30) Foreign Application Priority Data
Jul. 28, 2020   (EP) ..................................... 20382679

(51) Int. Cl.
*C12Q 1/6886* (2018.01)
*C12Q 1/6844* (2018.01)
(52) U.S. Cl.
CPC ......... *C12Q 1/6886* (2013.01); *C12Q 1/6844* (2013.01); *C12Q 2600/106* (2013.01); *C12Q 2600/118* (2013.01); *C12Q 2600/158* (2013.01)
(58) Field of Classification Search
CPC ............ C12Q 1/6886; C12Q 2600/118; C12Q 2600/158
See application file for complete search history.

(56) References Cited

U.S. PATENT DOCUMENTS

2009/0299640 A1* 12/2009 Ellis ..................... C12Q 1/6886
  702/19
2020/0071768 A1   3/2020 Cho et al.

FOREIGN PATENT DOCUMENTS

EP          2133433       12/2009
WO          2013177245    11/2013
WO          WO-2019232485 A1 * 12/2019   ......... G01N 33/5308

OTHER PUBLICATIONS

Harbig et al., "A sequence-based identification of the genes detected by probesets on the Affymetrix U133 plus 2.0 array," Nucleic Acids Research, vol. 33, No. 3, e31, pp. 1-9. (Year: 2005).*
Conte PF, Griguolo G, Dieci MV, et al. PAM50 HER2-enriched subtype as an independent prognostic factor in early- stage HER2+ breast cancer following adjuvant chemotherapy plus trastuzumab in the ShortHER trial. J Clin Oncol. 2019;37(suppl):abstr 544.
Anonymous: "Affymetrix GeneChip Human Genome U133 Array Set HGU133A", NCBI, Geo, Platform GPL96, Mar. 11, 2002, pp. 1-511.
Perez, Edith A., et al., "Trastuzumab Plus Adjuvant Chemotherapy for Human Epidermal Growth Factor Receptor 2-Positive Breast Cancer: Planned Joint Analysis of Overall Survival From NSABP B-31 and NCCTG N9831", Journal of Clinical Oncology, Nov. 20, 2014, vol. 22, No. 33, pp. 3744-3752.
Min, Kyueng-Whan, et al., "Diagnostic and Prognostic Relevance of MMP-11 Expression in the Stromal Fibroblast-Like Cells Adjacent to Invasive Ductal Carcinoma of the Breast", Annals of Surgical Oncology, Nov. 1, 2012, vol. 20, No. 53, pp. 433-442.
Cheng, Chun-Wen, et al., "The Clinical Implications of MMP-11 and CK-20 Expression in Human Breast Cancer", Clinical Chimica Acta, Feb. 1, 2010, vol. 411, No. 3-4, pp. 234-241.
Braunstein, Lior Z., et al., "Molecular Phenotype, Multigene Assays, and the Locoregional Management of Breast Cancer", Seminars in Radiation Oncology, Jan. 1, 2016, vol. 26, No. 1, pp. 9-16.
International Search Report and Written Opinion based on PCT International Application No. PCT/EP2021/070788, dated Nov. 9, 2021, pp. 1-17.

* cited by examiner

*Primary Examiner* — Young J Kim
(74) *Attorney, Agent, or Firm* — McCarter & English, LLC

(57)              ABSTRACT
The present invention refers to an in vitro method for the prognosis of patients suffering from HER2+ breast cancer and/or for the prediction of response to anti-HER2 therapies in patients suffering from HER2+ breast cancer.

2 Claims, 5 Drawing Sheets

A

B

B

IN VITRO METHOD FOR THE PROGNOSIS OF PATIENTS SUFFERING FROM HER2-POSITIVE BREAST CANCER

FIELD OF THE INVENTION

The present invention refers to the medical field. Particularly, the present invention refers to an in vitro method for the prognosis of patients suffering from HER2-positive (HER2+) breast cancer and/or for the prediction of response to anti-HER2 therapies in patients suffering from HER2+ breast cancer.

STATE OF THE ART

HER2-positive (HER2+) breast cancer represents 20% of all invasive breast carcinomas and is responsible for a substantial proportion of deaths. In early stages, (neo)adjuvant chemotherapy and anti-HER2 therapy (plus endocrine therapy in hormone receptor-positive disease) have consistently shown significant and long-term clinical benefits, in terms of disease-free survival (DFS) and overall survival [Perez E A, Romond E H, Suman V J, et al. *Trastuzumab Plus Adjuvant Chemotherapy for Human Epidermal Growth Factor Receptor 2—Positive Breast Cancer: Planned Joint Analysis of Overall Survival From NSABP B-31 and NCCTG N9831. Journal of Clinical Oncology* 2014; 32(33): 3744-52]. However, substantial heterogeneity exists in HER2+ disease regarding tumour biology, patient's prognosis and treatment benefit.

Strategies to either escalate or de-escalate systemic therapy in early-stage HER2+ disease have been explored, such as decreasing the amount of chemotherapy and the duration of trastuzumab or increasing HER2 blockade with pertuzumab, neratinib or switching the type of anti-HER2 therapy to T-DM1 in patients who did not achieve a pathological complete response (pCR) following neoadjuvant trastuzumab-based chemotherapy. Despite all these efforts to improve survival outcomes, the crude reality is that the vast majority of patients with early-stage HER2+ disease is cured with chemotherapy and trastuzumab [Conte P F, Griguolo G, Dieci M V et al. *PAM50 HER2-enriched subtype as an independent prognostic factor in early-stage HER2+ breast cancer following adjuvant chemotherapy plus trastuzumab in the ShortHER trial. Journal of Clinical Oncology* 2019; 37(15 suppl): 544-].

In early-stage hormone receptor-positive/HER2-negative disease, several prognostic tools allow a better individualization of systemic treatments and are widely available. For example, gene expression-based assays such as OncotypeDX or Mammaprint help identify low-risk patients who do not need (neo)adjuvant chemotherapy. Second generation genomic tests, such as PAM50/Prosigna, which include clinical parameters such as tumour size and nodal status in the final risk assessment, might better discriminate patients who may not need chemotherapy from those who are likely to benefit.

To date, several variables beyond the tumor-nodal-staging classification (i.e. TNM) have been associated with prognosis in early-stage HER2+ breast cancer. Examples are stromal tumour-infiltrating lymphocytes (TILs) and PAM50 subtypes. Similarly, these biomarkers and PIK3CA mutations have been associated with the probability to achieve a pCR, which is also associated with long-term outcome.

However, decisions today about escalation or de-escalation of systemic therapies are based on nodal status, hormone receptor status and therapy response.

Consequently, there is an unmet medical need of finding new tools focused on the prognosis of patients suffering from HER2+ breast cancer and the prediction of response to anti-HER2 therapies in this type of patients. In this context, the present invention is focused on solving this problem and it is herein provided a new tool which helps the clinicians to design guide-systemic therapies in early-stage HER2+ breast cancer.

DESCRIPTION OF THE INVENTION

Brief Description of the Invention

Such as it has been explained above, escalation or de-escalation of systemic therapy is a controversial topic in early-stage HER2+ breast cancer. Consequently, a prognostic assay for predicting survival outcome, particularly in newly diagnosed HER2+ breast cancer patients, is herein presented as an aid to treatment decisions, which is based on the combination of the following 17 variables: MMP11 gene, nodal status (pN1), tumor staging (pT2-4), PAM50 subtypes, CDC6 gene, CDH3 gene, TMEM45B gene, EXO1 gene, FGFR4 gene, RRM2 gene, tumor-infiltrating lymphocytes (TILs), MLPH gene, KRT5 gene, KRT14 gene, MYC gene, PHGDH gene and/or BAG1 gene.

To our knowledge, this is the first study attempting to build a combined prognostic score (called HER2DX) based on 17 clinicopathological and genomic variables in early-stage HER2+ breast cancer using tumour samples from a Phase III clinical trial. In addition, the prognostic score was evaluated in a combined neoadjuvant dataset of patients with newly diagnosed HER2+ breast cancer who received anti-HER2-based therapy, providing insights about the relationship between response to therapy in the neoadjuvant setting and long-term survival outcome. The evidence suggests that HER2DX identifies a substantial proportion of patients with early-stage HER2+ breast cancer who might not need additional therapies, such as pertuzumab, neratinib or T-DM1, due to their outstanding survival outcomes with chemotherapy and trastuzumab (plus endocrine therapy if hormonal receptor-positive). Further studies should establish the clinical utility of HER2DX in this context and explore its value to help further de-escalate systemic treatments such as the duration of trastuzumab and/or the amount of chemotherapy. Finally, multi-parameter prognostic models should be explored in other breast cancer subtypes, such as triple-negative disease, as well as other cancer-types.

Particularly, clinicopathological data, stromal tumour infiltrating-lymphocytes (TILs), PAM50 subtypes and expression of 55 genes were obtained from 435 patients who participated in the Short-HER phase III trial, which randomised patients to adjuvant anthracycline/taxane-based chemotherapy with either 3 or 12 months of trastuzumab. Variables associated with distant metastasis-free survival (DMFS) were used to build and test a combined prognostic model. The same model was evaluated in an independent combined dataset of 267 patients with early-stage HER2+ breast cancer treated with neoadjuvant anti-HER2-based therapy across 4 cohorts (Hospital Clinic and Padova University cohorts), including 2 trials (CHER-LOB and PAMELA).

In Short-HER (training cohort), tumour stage (T1 vs. rest), nodal stage (NO vs. rest), TILs (continuous variable), subtype (HER2-enriched and Basal-like vs. rest) and 13 genes composed the final model (HER2DX). HER2DX was significantly associated with DMFS as a continuous variable (p<0.001). Two cut-offs defined low-risk (50%), med-risk (25%) and high-risk (25%) populations. The 5-year DMFS of the low-, med- and high-risk populations were 98.1% (95% CI 96.3-99.9), 88.9% (83.2-95.0) and 73.9% (66.0-82.7), respectively (hazard ratio [HR] low- vs. high-risk=0.04, 0.0-0.1, p<0.001). In the evaluation cohort, HER2DX was significantly associated with disease-free survival (DFS) as a continuous variable (HR=2.77, 1.4-5.6, p=0.004) and as group categories (low- vs. high-risk HR=0.27, 0.1-0.7, p=0.005). The 5- and 8-year DFS of the HER2DX low-risk group was 93.5% (89.0-98.3%) and 91.7% (86.2-97.6%), respectively. The statistical results obtained for the model are summarize in Table 1.

TABLE 1

| Short-HER dataset | HR | 95% CI Low | 95% CI High | P-value | AUC ROC |
|---|---|---|---|---|---|
| All dataset | 2.232 | 4.934 | 19.176 | <0.0001 | 0.832 |

Kindly note that the model comprising 17 variables is the more specific embodiment of the present invention. However, in order to demonstrate that several combinations comprising less than 17 variables could also be used in the context of the present invention, the inventors of the present invention also analysed combination of biomarkers comprising up to 16 variables selected from the group comprising: MMP11 gene, nodal status (pN1), tumor staging (pT2-4), PAM50 subtypes, CDC6 gene, CDH3 gene, TMEM45B gene, EXO1 gene, FGFR4 gene, RRM2 gene, tumor-infiltrating lymphocytes (TILs), MLPH gene, KRT5 gene, KRT14 gene, MYC gene, PHGDH gene and/or BAG1 gene. These combinations are also included in the present invention for the prognosis of patients suffering from HER2+ breast cancer and/or for the prediction of response to anti-HER2 therapies in patients suffering from HER2+ breast cancer.

As an example, Table 2 shows the statistical results obtained with different combinations of 16 biomarkers (wherein the biomarker cited in the first column has been excluded from the signature):

TABLE 2

| Variable excluded | p-value | AUC ROC |
|---|---|---|
| MLPH | 9.38E−11 | 0.83312048 |
| TMEM45B | 1.17E−10 | 0.83258834 |
| RRM2 | 9.16E−11 | 0.8313112 |
| MYC | 8.31E−11 | 0.8305662 |
| EXO1 | 9.38E−11 | 0.83024691 |
| CallHER2Basal | 7.75E−11 | 0.83014049 |
| KRT5 | 9.79E−11 | 0.82928906 |
| PHGDH | 1.72E−10 | 0.82875692 |
| KRT14 | 9.41E−11 | 0.82811835 |
| FGFR4 | 1.43E−10 | 0.82801192 |
| CDC6 | 1.29E−10 | 0.82790549 |
| CDH3 | 1.35E−10 | 0.82758621 |
| pT1vsrest | 1.70E−10 | 0.82237122 |
| TILS | 2.65E−10 | 0.82045551 |
| BAG1 | 3.22E−10 | 0.81683695 |
| MMP11 | 6.23E−10 | 0.8117284 |
| pN1 | 3.19E−09 | 0.80140485 |

Moreover, Table 3 shows more examples of combinations of 15 biomarkers (wherein the biomarkers cited in the first column has been excluded from the biosignature):

TABLE 3

| Variable excluded | p-value | AUC ROC |
|---|---|---|
| BAG1_CallHER2Basal | 3.48E−10 | 0.81226054 |
| BAG1_CDC6 | 3.24E−10 | 0.81598553 |
| BAG1_CDH3 | 5.81E−10 | 0.81087697 |
| BAG1_EXO1 | 2.97E−10 | 0.8166241 |
| BAG1_FGFR4 | 4.98E−10 | 0.81156875 |
| BAG1_KRT14 | 3.66E−10 | 0.81146232 |
| BAG1_KRT5 | 3.52E−10 | 0.81204768 |
| BAG1_MLPH | 3.74E−10 | 0.81534696 |
| BAG1_MMP11 | 2.19E−09 | 0.79374202 |
| BAG1_MYC | 3.34E−10 | 0.81577267 |
| BAG1_PHGDH | 4.75E−10 | 0.81321839 |
| BAG1_pN01 | 1.01E−08 | 0.78224777 |
| BAG1_pT1vsrest | 7.02E−10 | 0.80630055 |
| BAG1_RRM2 | 3.17E−10 | 0.81641124 |
| BAG1_TILS | 7.22E−10 | 0.80906769 |
| BAG1_TMEM45B | 4.09E−10 | 0.81332482 |
| CallHER2Basal_BAG1 | 3.48E−10 | 0.81226054 |
| CallHER2Basal_CDC6 | 1.29E−10 | 0.82396765 |
| CallHER2Basal_CDH3 | 1.29E−10 | 0.82109408 |
| CallHER2Basal_EXO1 | 7.85E−11 | 0.82886335 |
| CallHER2Basal_FGFR4 | 1.25E−10 | 0.82460622 |
| CallHER2Basal_KRT14 | 8.22E−11 | 0.8249255 |
| CallHER2Basal_KRT5 | 8.18E−11 | 0.82811835 |
| CallHER2Basal_MLPH | 8.12E−11 | 0.83014049 |
| CallHER2Basal_MMP11 | 6.60E−10 | 0.80768412 |
| CallHER2Basal_MYC | 7.20E−11 | 0.82875692 |
| CallHER2Basal_PHGDH | 1.31E−10 | 0.82811835 |
| CallHER2Basal_pN0_1 | 2.04E−09 | 0.80193699 |
| CallHER2Basal_pT1vsrest | 1.28E−10 | 0.82269051 |
| CallHER2Basal_RRM2 | 7.64E−11 | 0.82896977 |
| CallHER2Basal_TILS | 1.75E−10 | 0.82162622 |
| CallHER2Basal_TMEM45B | 1.01E−10 | 0.82694764 |
| CDC6_BAG1 | 3.24E−10 | 0.81598553 |
| CDC6_CallHER2Basal | 1.29E−10 | 0.82396765 |
| CDC6_CDH3 | 1.94E−10 | 0.82460622 |
| CDC6_EXO1 | 1.42E−10 | 0.82779906 |
| CDC6_FGFR4 | 2.13E−10 | 0.82290336 |
| CDC6_KRT14 | 1.45E−10 | 0.82396765 |
| CDC6_KRT5 | 1.49E−10 | 0.82364836 |
| CDC6_MLPH | 1.20E−10 | 0.82960834 |
| CDC6_MMP11 | 1.01E−09 | 0.80938697 |
| CDC6_MYC | 1.17E−10 | 0.82896977 |
| CDC6_PHGDH | 2.37E−10 | 0.82428693 |
| CDC6_pN0_1 | 8.12E−09 | 0.79326309 |
| CDC6_pT1vsrest | 2.53E−10 | 0.81502767 |
| CDC6_RRM2 | 1.27E−10 | 0.82790549 |
| CDC6_TILS | 4.37E−10 | 0.81683695 |
| CDC6_TMEM45B | 1.62E−10 | 0.82428693 |
| CDH3_BAG1 | 5.81E−10 | 0.81087697 |
| CDH3_CallHER2Basal | 1.29E−10 | 0.82109408 |
| CDH3_CDC6 | 1.94E−10 | 0.82460622 |
| CDH3_EXO1 | 1.37E−10 | 0.82790549 |
| CDH3_FGFR4 | 2.18E−10 | 0.82173265 |
| CDH3_KRT14 | 1.34E−10 | 0.82364836 |
| CDH3_KRT5 | 1.32E−10 | 0.8256705 |
| CDH3_MLPH | 1.46E−10 | 0.82705407 |
| CDH3_MMP11 | 1.07E−09 | 0.79767986 |
| CDH3_MYC | 1.24E−10 | 0.82758621 |
| CDH3_PHGDH | 2.17E−10 | 0.82354193 |
| CDH3_pN0_1 | 4.18E−09 | 0.79565773 |
| CDH3_pT1vsrest | 2.63E−10 | 0.82088123 |
| CDH3_RRM2 | 1.33E−10 | 0.82801192 |
| CDH3_TILS | 3.20E−10 | 0.81694338 |
| CDH3_TMEM45B | 1.74E−10 | 0.8249255 |
| EXO1_BAG1 | 2.97E−10 | 0.8166241 |
| EXO1_CallHER2Basal | 7.85E−11 | 0.82886335 |
| EXO1_CDC6 | 1.42E−10 | 0.82779906 |
| EXO1_CDH3 | 1.37E−10 | 0.82790549 |
| EXO1_FGFR4 | 1.44E−10 | 0.82609621 |
| EXO1_KRT14 | 9.45E−11 | 0.82652192 |
| EXO1_KRT5 | 9.72E−11 | 0.82918263 |
| EXO1_MLPH | 9.25E−11 | 0.83088548 |
| EXO1_MMP11 | 6.07E−10 | 0.81289911 |
| EXO1_MYC | 8.31E−11 | 0.83099191 |
| EXO1_PHGDH | 1.70E−10 | 0.82779906 |
| EXO1_pN0_1 | 3.24E−09 | 0.79980843 |
| EXO1_pT1vsrest | 1.68E−10 | 0.82205194 |
| EXO1_RRM2 | 9.16E−11 | 0.83024691 |

TABLE 3-continued

| Variable excluded | p-value | AUC ROC |
|---|---|---|
| EXO1__TILS | 2.63E-10 | 0.82056194 |
| EXO1__TMEM45B | 1.17E-10 | 0.83109834 |
| FGFR4__BAG1 | 4.98E-10 | 0.81156875 |
| FGFR4__CallHER2Basal | 1.25E-10 | 0.82460622 |
| FGFR4__CDC6 | 2.13E-10 | 0.82290336 |
| FGFR4__CDH3 | 2.18E-10 | 0.82173265 |
| FGFR4__EXO1 | 1.44E-10 | 0.82609621 |
| FGFR4__KRT14 | 1.45E-10 | 0.82354193 |
| FGFR4__KRT5 | 1.51E-10 | 0.82449979 |
| FGFR4__MLPH | 1.42E-10 | 0.82673478 |
| FGFR4__MMP11 | 9.84E-10 | 0.80523627 |
| FGFR4__MYC | 1.26E-10 | 0.82673478 |
| FGFR4__PHGDH | 2.52E-10 | 0.82396765 |
| FGFR4__pN0__1 | 4.70E-09 | 0.7955513 |
| FGFR4__pT1vsrest | 2.62E-10 | 0.81832695 |
| FGFR4__RRM2 | 1.40E-10 | 0.8283312 |
| FGFR4__TILS | 3.93E-10 | 0.81630481 |
| FGFR4__TMEM45B | 1.78E-10 | 0.82620264 |
| KRT14__BAG1 | 3.66E-10 | 0.81146232 |
| KRT14__CallHER2Basal | 8.22E-11 | 0.8249255 |
| KRT14__CDC6 | 1.45E-10 | 0.82396765 |
| KRT14__CDH3 | 1.34E-10 | 0.82364836 |
| KRT14__EXO1 | 9.45E-11 | 0.82652192 |
| KRT14__FGFR4 | 1.45E-10 | 0.82354193 |
| KRT14__KRT5 | 1.21E-10 | 0.82311622 |
| KRT14__MLPH | 9.54E-11 | 0.82790549 |
| KRT14__MMP11 | 7.00E-10 | 0.80725841 |
| KRT14__MYC | 8.71E-11 | 0.82716049 |
| KRT14__PHGDH | 1.80E-10 | 0.82290336 |
| KRT14__pN0__1 | 3.53E-09 | 0.79810558 |
| KRT14__pT1vsrest | 2.10E-10 | 0.81694338 |
| KRT14__RRM2 | 9.19E-11 | 0.82716049 |
| KRT14__TILS | 2.58E-10 | 0.81939123 |
| KRT14__TMEM45B | 1.14E-10 | 0.82620264 |
| KRT5__BAG1 | 3.52E-10 | 0.81204768 |
| KRT5__CallHER2Basal | 8.18E-11 | 0.82811835 |
| KRT5__CDC6 | 1.49E-10 | 0.82364836 |
| KRT5__CDH3 | 1.32E-10 | 0.8256705 |
| KRT5__EXO1 | 9.72E-11 | 0.82918263 |
| KRT5__FGFR4 | 1.51E-10 | 0.82449979 |
| KRT5__KRT14 | 1.21E-10 | 0.82311622 |
| KRT5__MLPH | 9.70E-11 | 0.82875692 |
| KRT5__MMP11 | 7.88E-10 | 0.80928054 |
| KRT5__MYC | 8.84E-11 | 0.82747978 |
| KRT5__PHGDH | 1.88E-10 | 0.82300979 |
| KRT5__pN0__1 | 3.64E-09 | 0.80087271 |
| KRT5__pT1vsrest | 2.01E-10 | 0.81630481 |
| KRT5__RRM2 | 9.53E-11 | 0.82971477 |
| KRT5__TILS | 2.96E-10 | 0.81832695 |
| KRT5__TMEM45B | 1.20E-10 | 0.82694764 |
| MLPH__BAG1 | 3.74E-10 | 0.81534696 |
| MLPH__CallHER2Basal | 8.12E-11 | 0.83014049 |
| MLPH__CDC6 | 1.20E-10 | 0.82960834 |
| MLPH__CDH3 | 1.46E-10 | 0.82705407 |
| MLPH__EXO1 | 9.25E-11 | 0.83088548 |
| MLPH__FGFR4 | 1.42E-10 | 0.82673478 |
| MLPH__KRT14 | 9.54E-11 | 0.82790549 |
| MLPH__KRT5 | 9.70E-11 | 0.82875692 |
| MLPH__MMP11 | 6.02E-10 | 0.81002554 |
| MLPH__MYC | 8.41E-11 | 0.83205619 |
| MLPH__PHGDH | 1.65E-10 | 0.82875692 |
| MLPH__pN0__1 | 2.88E-09 | 0.80214985 |
| MLPH__pT1vsrest | 1.71E-10 | 0.82311622 |
| MLPH__RRM2 | 9.15E-11 | 0.83184334 |
| MLPH__TILS | 2.42E-11 | 0.82194551 |
| MLPH__TMEM45B | 1.16E-10 | 0.83173691 |
| MMP11__BAG1 | 2.19E-09 | 0.79374202 |
| MMP11__CallHER2Basal | 6.60E-10 | 0.80768412 |
| MMP11__CDC6 | 1.01E-09 | 0.80938697 |
| MMP11__CDH3 | 1.07E-09 | 0.79767986 |
| MMP11__EXO1 | 6.07E-10 | 0.81289911 |
| MMP11__FGFR4 | 9.84E-10 | 0.80523627 |
| MMP11__KRT14 | 7.00E-10 | 0.80725841 |
| MMP11__KRT5 | 7.88E-10 | 0.80928054 |
| MMP11__MLPH | 6.02E-10 | 0.81002554 |
| MMP11__MYC | 5.26E-10 | 0.81332482 |
| MMP11__PHGDH | 1.72E-09 | 0.80321413 |
| MMP11__pN0__1 | 3.14E-08 | 0.77692635 |

TABLE 3-continued

| Variable excluded | p-value | AUC ROC |
|---|---|---|
| MMP11__pT1vsrest | 1.04E-09 | 0.80449127 |
| MMP11__RRM2 | 5.91E-10 | 0.81119625 |
| MMP11__TILS | 4.26E-09 | 0.79012346 |
| MMP11__TMEM45B | 9.73E-10 | 0.80619413 |
| MYC__BAG1 | 3.34E-10 | 0.81577267 |
| MYC__CallHER2Basal | 7.20E-11 | 0.82875692 |
| MYC__CDC6 | 1.17E-10 | 0.82896977 |
| MYC__CDH3 | 1.24E-10 | 0.82758621 |
| MYC__EXO1 | 8.31E-11 | 0.83099191 |
| MYC__FGFR4 | 1.26E-10 | 0.82673478 |
| MYC__KRT14 | 8.71E-11 | 0.82716049 |
| MYC__KRT5 | 8.84E-11 | 0.82747978 |
| MYC__MLPH | 8.41E-11 | 0.83205619 |
| MYC__MMP11 | 5.26E-10 | 0.81332482 |
| MYC__PHGDH | 1.50E-10 | 0.82609621 |
| MYC__pN0__1 | 2.49E-09 | 0.80204342 |
| MYC__pT1vsrest | 1.47E-10 | 0.82056194 |
| MYC__RRM2 | 8.09E-11 | 0.83067263 |
| MYC__TILS | 2.24E-10 | 0.82258408 |
| MYC__TMEM45B | 1.05E-10 | 0.82790549 |
| PHGDH__BAG1 | 4.75E-10 | 0.81321839 |
| PHGDH__CallHER2Basal | 1.31E-10 | 0.82811835 |
| PHGDH__CDC6 | 2.37E-10 | 0.82428693 |
| PHGDH__CDH3 | 2.17E-10 | 0.82354193 |
| PHGDH__EXO1 | 1.70E-10 | 0.82779906 |
| PHGDH__FGFR4 | 2.52E-10 | 0.82396765 |
| PHGDH__KRT14 | 1.80E-10 | 0.82290336 |
| PHGDH__KRT5 | 1.88E-10 | 0.82300979 |
| PHGDH__MLPH | 1.65E-10 | 0.82875692 |
| PHGDH__MMP11 | 1.72E-09 | 0.80321413 |
| PHGDH__MYC | 1.50E-10 | 0.82609621 |
| PHGDH__pN0__1 | 6.74E-09 | 0.79661558 |
| PHGDH__pT1vsrest | 3.31E-10 | 0.81577267 |
| PHGDH__RRM2 | 1.66E-10 | 0.82875692 |
| PHGDH__TILS | 5.56E-10 | 0.81715624 |
| PHGDH__TMEM45B | 2.09E-10 | 0.8241805 |
| pN0__1__BAG1 | 1.01E-08 | 0.78224777 |
| pN0__1__CallHER2Basal | 2.04E-09 | 0.80193699 |
| pN0__1__CDC6 | 8.12E-09 | 0.79326309 |
| pN0__1__CDH3 | 4.18E-09 | 0.79565773 |
| pN0__1__EXO1 | 3.24E-09 | 0.79980843 |
| pN0__1__FGFR4 | 4.70E-09 | 0.7955513 |
| pN0__1__KRT14 | 3.53E-09 | 0.79810558 |
| pN0__1__KRT5 | 3.64E-09 | 0.80087271 |
| pN0__1__MLPH | 2.88E-09 | 0.80214985 |
| pN0__1__MMP11 | 3.14E-08 | 0.77692635 |
| pN0__1__MYC | 2.49E-09 | 0.80204342 |
| pN0__1__PHGDH | 6.74E-09 | 0.79661558 |
| pN0__1__pT1vsrest | 1.35E-08 | 0.7793742 |
| pN0__1__RRM2 | 3.12E-09 | 0.80055343 |
| pN0__1__TILS | 1.37E-08 | 0.7850149 |
| pN0__1__TMEM45B | 3.21E-09 | 0.80353342 |
| pT1vsrest__BAG1 | 7.02E-10 | 0.80630055 |
| pT1vsrest__CallHER2Basal | 1.28E-10 | 0.82269051 |
| pT1vsrest__CDC6 | 2.53E-10 | 0.81502767 |
| pT1vsrest__CDH3 | 2.63E-10 | 0.82088123 |
| pT1vsrest__EXO1 | 1.68E-10 | 0.82205194 |
| pT1vsrest__FGFR4 | 2.62E-10 | 0.81832695 |
| pT1vsrest__KRT14 | 2.10E-10 | 0.81694338 |
| pT1vsrest__KRT5 | 2.01E-10 | 0.81630481 |
| pT1vsrest__MLPH | 1.71E-10 | 0.82311622 |
| pT1vsrest__MMP11 | 1.04E-09 | 0.80449127 |
| pT1vsrest__MYC | 1.47E-10 | 0.82056194 |
| pT1vsrest__PHGDH | 3.31E-10 | 0.81577267 |
| pT1vsrest__pN0__1 | 1.35E-08 | 0.7793742 |
| pT1vsrest__RRM2 | 1.67E-10 | 0.82258408 |
| pT1vsrest__TILS | 5.34E-10 | 0.80736484 |
| pT1vsrest__TMEM45B | 2.03E-10 | 0.82503193 |
| RRM2__BAG1 | 3.17E-10 | 0.81641124 |
| RRM2__CallHER2Basal | 7.64E-11 | 0.82896977 |
| RRM2__CDC6 | 1.27E-10 | 0.82790549 |
| RRM2__CDH3 | 1.33E-10 | 0.82801192 |
| RRM2__EXO1 | 9.16E-11 | 0.83024691 |
| RRM2__FGFR4 | 1.40E-10 | 0.8283312 |
| RRM2__KRT14 | 9.19E-11 | 0.82716049 |
| RRM2__KRT5 | 9.53E-11 | 0.82971477 |
| RRM2__MLPH | 9.15E-11 | 0.83184334 |
| RRM2__MMP11 | 5.91E-10 | 0.81119625 |

TABLE 3-continued

| Variable excluded | p-value | AUC ROC |
|---|---|---|
| RRM2_MYC | 8.09E−11 | 0.83067263 |
| RRM2_PHGDH | 1.66E−10 | 0.82875692 |
| RRM2_pN0_1 | 3.12E−09 | 0.80055343 |
| RRM2_pT1vsrest | 1.67E−10 | 0.82258408 |
| RRM2_TILS | 2.54E−10 | 0.82034908 |
| RRM2_TMEM45B | 1.13E−10 | 0.83301405 |
| TILS_BAG1 | 7.22E−10 | 0.80906769 |
| TILS_CallHER2Basal | 1.75E−10 | 0.82162622 |
| TILS_CDC6 | 4.37E−10 | 0.81683695 |
| TILS_CDH3 | 3.20E−10 | 0.81694338 |
| TILS_EXO1 | 2.63E−10 | 0.82056194 |
| TILS_FGFR4 | 3.93E−10 | 0.81630481 |
| TILS_KRT14 | 2.58E−10 | 0.81939123 |
| TILS_KRT5 | 2.96E−10 | 0.81832695 |
| TILS_MLPH | 2.42E−10 | 0.82194551 |
| TILS_MMP11 | 4.26E−09 | 0.79012346 |
| TILS_MYC | 2.24E−10 | 0.82258408 |
| TILS_PHGDH | 5.56E−10 | 0.81715624 |
| TILS_pN0_1 | 1.37E−08 | 0.7850149 |
| TILS_pT1vsrest | 5.34E−10 | 0.80736484 |
| TILS_RRM2 | 2.54E−10 | 0.82034908 |
| TILS_TMEM45B | 3.28E−10 | 0.82098765 |
| TMEM45B_BAG1 | 4.09E−10 | 0.81332482 |
| TMEM45B_CallHER2Basal | 1.01E−10 | 0.82694764 |
| TMEM45B_CDC6 | 1.62E−10 | 0.82428693 |
| TMEM45B_CDH3 | 1.74E−10 | 0.8249255 |
| TMEM45B_EXO1 | 1.17E−10 | 0.83109834 |
| TMEM45B_FGFR4 | 1.78E−10 | 0.82620264 |
| TMEM45B_KRT14 | 1.14E−10 | 0.82620264 |
| TMEM45B_KRT5 | 1.20E−10 | 0.82694764 |
| TMEM45B_MLPH | 1.16E−10 | 0.83173691 |
| TMEM45B_MMP11 | 9.73E−10 | 0.80619413 |
| TMEM45B_MYC | 1.05E−10 | 0.82790549 |
| TMEM45B_PHGDH | 2.09E−10 | 0.8241805 |
| TMEM45B_pN0_1 | 3.21E−09 | 0.80353342 |
| TMEM45B_pT1vsrest | 2.03E−10 | 0.82503193 |
| TMEM45B_RRM2 | 1.13E−10 | 0.83301405 |
| TMEM45B_TILS | 3.28E−10 | 0.82098765 |

Finally, the individual performance of each of the variables included in the model was analysed and it was confirmed that any of the 13 genes included in the model (MMP11, CDC6, CDH3, TMEM45B, EXO1, FGFR4, RRM2, MLPH, KRT5, KRT14, MYC, PHGDH or BAG1) can be individually used for the prognosis of patients suffering from HER2+ breast cancer and/or for the prediction of response to anti-HER2 therapies in patients suffering from HER2+ breast cancer. After analysing the genes in isolation, it was elected MMP11 as the starting point, which is present in several signatures which show high AUC values. In any case, any of the other 12 genes (CDC6, CDH3, TMEM45B, EXO1, FGFR4, RRM2, MLPH, KRT5, KRT14, MYC, PHGDH or BAG1) could be also used for the purpose described in the present invention (see Table 4).

TABLE 4

| Biomarker | Survival Coefficient | Univariate Hazard ratio DMFS |
|---|---|---|
| MMP11 | 0.2 | 1.89 |
| CDC6 | 0.087 | 1.28 |
| CDH3 | 0.076 | 1.18 |
| TMEM45B | 0.048 | 1.3 |
| EXO1 | 0.024 | 1.14 |
| FGFR4 | 0.021 | 1.17 |
| RRM2 | 0.008 | 1.2 |
| MLPH | −0.022 | 0.96 |
| KRT5 | −0.024 | 0.76 |
| KRT14 | −0.04 | 0.75 |
| MYC | −0.05 | 0.75 |
| PHGDH | −0.05 | 0.87 |
| BAG1 | −0.168 | 0.75 |

So, the first embodiment of the present invention refers to an in vitro method for the prognosis of patients suffering from HER2+ breast cancer, which comprises measuring the level of expression of the gene MMP11 in a biological sample obtained from the patient, wherein a higher expression level of the gene MMP11, with respect to a pre-established reference level of expression (geomean of the housekeeping genes [ACTB, MRPL19, PSMC4, RPLP0 and SF3A1]) measured in the same patient, is indicative of bad prognosis, or wherein a lower expression level of the gene MMP11, with respect to said pre-established reference level of expression measured in control patients, is indicative of good prognosis.

The second embodiment of the present invention refers to an in vitro method for the prediction of response to anti-HER2 therapies in patients suffering from HER2+ breast cancer, or for classifying patients into responder or non-responder patients to anti-HER2 therapies, which comprises measuring the level of expression of the gene MMP11 in a biological sample obtained from the patient, wherein a higher expression level of the gene MMP11, with respect to said pre-established reference level of expression, is indicative that the patient is a responder patient to anti-HER2 therapies, or wherein a lower expression level of the gene MMP11, with respect to said pre-established reference level of expression, is indicative that the patient is a non-responder patient to anti-HER2 therapies.

In a preferred embodiment, the above methods further comprises identifying the nodal status (pN1), tumor staging (pT2-4) or PAM50 subtypes, or measuring the level of expression of any to the following genes: CDC6, CDH3, TMEM45B, EXO1, FGFR4 and/or RRM2, wherein the identification of nodal status N1-3, tumor status T2-4, Non-luminal PAM50 (HER2-E and Basal-like), or a higher expression level of the genes CDC6, CDH3, TMEM45B, EXO1, FGFR4 and/or RRM2, with respect to said pre-established reference level of expression, is indicative of bad prognosis or that the patient is a responder patient to anti-HER2 therapies, or wherein the identification of nodal status N0, tumor status T1, PAM50 Luminal (non-HER2-E and non-Basal-like), or a lower expression level of the gene CDC6, CDH3, TMEM45B, EXO1, FGFR4 and/or RRM2, with respect to said pre-established reference level of expression, is indicative of good prognosis or that the patient is a non-responder patient to anti-HER2 therapies.

In a preferred embodiment, the above methods further comprises the identification of TILs or measuring the level of expression of any to the following genes: MLPH, KRT5, KRT14, MYC, PHGDH and/or BAG1, wherein a lower proportion of TILs or a lower expression level of the genes MLPH, KRT5, KRT14, MYC, PHGDH and/or BAG1, with respect to said pre-established reference level of expression, is indicative of bad prognosis or that the patient is a responder patient to anti-HER2 therapies, or wherein a higher proportion of TILs or a higher expression level of the genes MLPH, KRT5, KRT14, MYC, PHGDH and/or BAG1, with respect to said pre-established reference level of expression, is indicative of good prognosis or that the patient is a non-responder patient to anti-HER2 therapies.

In a preferred embodiment, the patient is suffering from early-stage HER2+ breast cancer.

In a preferred embodiment the biological sample is selected form: tissue, blood, serum or plasma.

In a preferred embodiment anti-HER2 therapy is a drug selected from: trastuzumab, pertuzumab, lapatinib, pyrotinib, poziotinib, tucatinib, neratinib, DS-8201a, SYD985 or ado-trastuzumab emtansine.

The third embodiment of the present invention refers to the in vitro use of MMP11 for the prognosis of patients suffering from HER2+ breast cancer, for the prediction of response to anti-HER2 therapies in patients suffering from HER2+ breast cancer, or for classifying patients into responder or non-responder patients to anti-HER2 therapies.

In a preferred embodiment, the present invention refers to the in vitro use of MMP11 for the prognosis of patients suffering from HER2+ breast cancer, for the prediction of response to anti-HER2 therapies in patients suffering from HER2+ breast cancer, or for classifying patients into responder or non-responder patients to anti-HER2 therapies, in combination with any of the following variables: pN1, pT2-4, PAM50 subtypes, CDC6, CDH3, TMEM45B, EXO1, FGFR4, RRM2, TILs, MLPH, KRT5, KRT14, MYC, PHGDH and/or BAG1.

The fourth embodiment of the present invention refers to the use of a kit comprising tools or reagents for measuring the level of expression of MMP11 for the prognosis of patients suffering from HER2+ breast cancer, for the prediction of response to anti-HER2 therapies in patients suffering from HER2+ breast cancer, or for classifying patients into responder or non-responder patients to anti-HER2 therapies.

In a preferred embodiment, the present invention refers to the use of a kit comprising tools or reagents for measuring the level of expression of MMP11 for the prognosis of patients suffering from HER2+ breast cancer, for the prediction of response to anti-HER2 therapies in patients suffering from HER2+ breast cancer, or for classifying patients into responder or non-responder patients to anti-HER2 therapies, further comprising tools or reagents for identifying the nodal status (pN1), tumor staging (pT2-4), PAM50 subtypes, or TILs; or for measuring the level of expression of any of the following genes: CDC6, CDH3, TMEM45B, EXO1, FGFR4, RRM2, MLPH, KRT5, KRT14, MYC, PHGDH and/or BAG1.

The fifth embodiment of the present invention refers to a kit performing any of the above mentioned methods which comprises: tools or reagents for obtaining a biological sample from the patients, selected from: tissue, blood, serum or plasma, and tools or reagents for identifying the nodal status (pN1), tumor staging (pT2-4) or PAM50 subtypes, for the identification and quantification of TILs; or for measuring the level of expression of any of the following genes: CDC6, CDH3, TMEM45B, EXO1, FGFR4, RRM2, MLPH, KRT5, KRT14, MYC, PHGDH and/or BAG1.

The sixth embodiment of the present invention refers to anti-HER2 therapy, or any pharmaceutical composition comprising thereof, optionally including pharmaceutically acceptable excipients or carriers, for use in the treatment of patients suffering from HER2+ breast cancer wherein the patient has been classified as responder patient following any of the above-cited methods. In a preferred embodiment, the anti-HER2 therapy is selected from: trastuzumab, pertuzumab, lapatinib, pyrotinib, poziotinib, tucatinib, neratinib, DS-8201a, SYD985 or ado-trastuzumab emtansine. In this sense, the present invention also refers to a method for treating a patient suffering from HER2+ breast cancer which comprised the administration of a therapeutically effective dose or amount of anti-HER2 compound, once the patient has been previously classified as responder patient following any of the above-cited methods.

The present invention also refers to the following the topics included below.

A method for detecting biomarkers in a test sample from a human subject suffering from HER2+ breast cancer, the method comprising:
- a) Contacting the test sample with a primer specific to the genes [MMP11, CDC6, CDH3, TMEM45B, EXO1, FGFR4, RRM2, MLPH, KRT5, KRT14, MYC, PHGDH and BAG1];
- b) amplifying to produce an amplification product in the test sample; and
- c) measuring the expression level by determining the level of the amplification product in the test sample.

In a preferred embodiment, the present invention is a computer-implemented invention, wherein a processing unit (hardware) and a software are configured to:
- a) Receive expression level values of the genes [MMP11, CDC6, CDH3, TMEM45B, EXO1, FGFR4, RRM2, MLPH, KRT5, KRT14, MYC, PHGDH and BAG1],
- b) Process the expression level values received for finding substantial variations or deviations, and
- c) Provide an output through a terminal display of the variation or deviation of the expression level, wherein the variation or deviation of the expression level indicates whether the patient has a good or bad prognosis. Particularly, a higher expression level of the genes [MMP11, CDC6, CDH3, TMEM45B, EXO1, FGFR4 and RRM2]; and a lower expression level of the genes [MLPH, KRT5, KRT14, MYC, PHGDH and BAG1], with respect to a pre-established reference level of expression, is indicative of bad prognosis, or a lower expression level of the genes [MMP11, CDC6, CDH3, TMEM45B, EXO1, FGFR4 and RRM2]; and a higher expression level of the genes [MLPH, KRT5, KRT14, MYC, PHGDH and BAG], with respect to a pre-established the reference level of expression, is indicative of good prognosis. On the other hand, a higher expression level of the genes [MMP11, CDC6, CDH3, TMEM45B, EXO1, FGFR4 and RRM2]; and a lower expression level of the genes [MLPH, KRT5, KRT14, MYC, PHGDH and BAG1], with respect to a pre-established reference level of expression, is indicative that the patient is a responder patient to anti-HER2 therapies, or a lower expression level of the genes [MMP11, CDC6, CDH3, TMEM45B, EXO1, FGFR4 and RRM2]; and a higher expression level of the genes [MLPH, KRT5, KRT14, MYC, PHGDH and BAG1], with respect to a pre-established reference level of expression, is indicative that the patient is a non-responder patient to anti-HER2 therapies.

Finally, the present invention also refers to a computer program or a computer-readable media containing means for carrying out a method defined above.

For the purpose of the present invention the following terms are defined:

The term "reference level of expression measured", when referring to the level of the biomarkers described in the present invention, refers to the geometric mean level of the 5 house-keeping genes observed in the patients, namely: ACTB, MRPL19, PSMC4, RPLP0 and SF3A1. A "reference" value can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data.

By the term "comprising" is meant the inclusion, without limitation, of whatever follows the word "comprising". Thus, use of the term "comprising" indicates that the listed elements are required or mandatory, but that other elements are optional and may or may not be present.

By "consisting of" is meant the inclusion, with limitation to whatever follows the phrase "consisting of". Thus, the phrase "consisting of" indicates that the listed elements are required or mandatory, and that no other elements may be present.

"Pharmaceutically acceptable excipient or carrier" refers to an excipient that may optionally be included in the compositions of the invention and that causes no significant adverse toxicological effects to the patient.

By "therapeutically effective dose or amount" of a composition is intended an amount that, when administered as described herein, brings about a positive therapeutic response in a subject having HER2+ breast cancer. The exact amount required will vary from subject to subject, depending on the age, and general condition of the subject, the severity of the condition being treated, mode of administration, and the like. An appropriate "effective" amount in any individual case may be determined by one of ordinary skill in the art using routine experimentation, based upon the information provided herein.

DETAILED DESCRIPTION OF THE INVENTION

Figure 1:
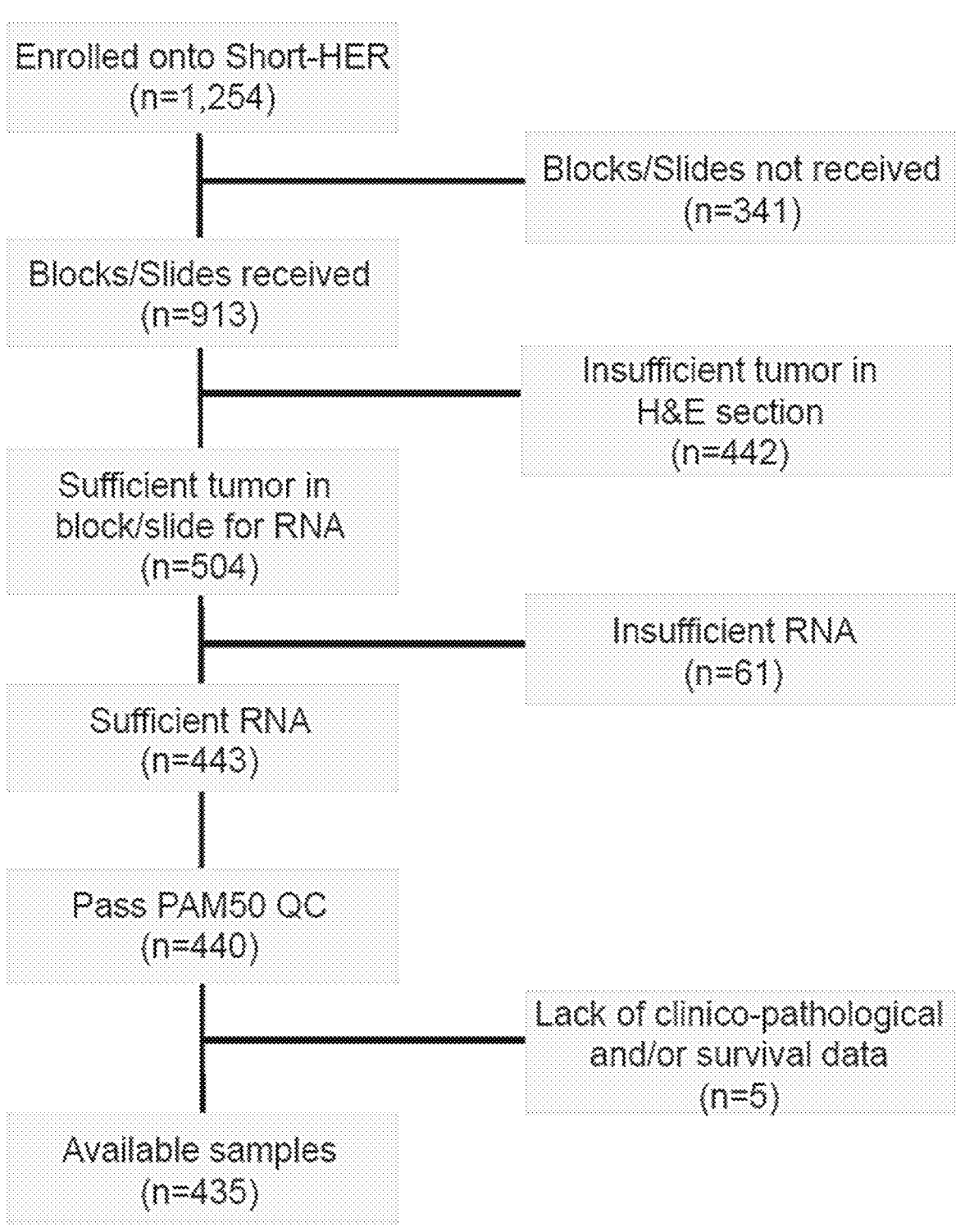
FIG. 1. Short-HER CONSORT diagram.

The present invention is specifically illustrated by means of the following examples without the intention of limiting the scope of protection to what it is described therein.

Example 1. Methods

Example 1.1. Study Designs

Short-HER was a randomized, multicentric, investigator-driven phase 3 study, aimed to assess the non-inferiority in terms of DFS of 9 weeks versus 1 year of adjuvant trastuzumab combined with chemotherapy. Briefly, women aged 18-75 with surgically resected, HER2+ breast cancer, suitable for adjuvant chemotherapy were eligible. Women had to have node positivity, or in case of node-negativity, at least one of the following features: tumour size >2 cm, grade 3, presence of lympho-vascular invasion, Ki67>20%, age ≤35 years or hormone receptor negativity. Patients with stage IIIB/IV disease were not eligible. A total of 1,254 patients with a performance status of 0-1 were randomised from 17 Dec. 2007 to 6 Oct. 2013 to arm A or arm B. Chemotherapy in arm A (long) consisted of adriamycin 60 mg/m$^2$ plus cyclophosphamide 600 mg/m$^2$ or epirubicin 90 mg/m$^2$ plus cyclophosphamide 600 mg/m$^2$ every 3 weeks for 4 courses followed by paclitaxel 175 mg/m$^2$ or docetaxel 100 mg/m$^2$ every 3 weeks for 4 courses. Trastuzumab was administered every 3 weeks for 18 doses, starting with the first taxane dose. Chemotherapy in arm B (short) consisted of docetaxel 100 mg/m$^2$ every 3 weeks for 3 courses followed by 5-fluorouracil 600 mg/m$^2$, epirubicin 60 mg/m$^2$, cyclophosphamide 600 mg/m$^2$ every 3 weeks for 3 courses. Trastuzumab was administered weekly for 9 weeks, starting concomitantly with docetaxel. When indicated, radiation and hormonal therapy were carried out according to local standard. Median follow-up was 91.4 months (IQR 75.1-105.6). In Short-HER, DMFS was an exploratory endpoint.

CHER-LOB was a randomised, noncomparative, investigator-driven phase 2 study from 8 Aug. 2006 to 25 Nov. 2010 of preoperative taxane-anthracycline consisting of paclitaxel (80 mg/m$^2$) for 12 weeks followed by fluorouracil, epirubicin, and cyclophosphamide for 4 courses every 3 weeks, in combination with trastuzumab (for 26 weeks), lapatinib (1,500 mg orally daily for 26 weeks) or combined trastuzumab plus lapatinib (1,000 mg daily for 26 weeks) in patients with HER2+, stage II to IIIA operable breast cancer and with a performance status of 0-1. The primary aim was to estimate the percentage of pCR. Treatment after surgery was left to treating physician discretion. Median follow-up was 60.0 months (IQR 46.9-69.4). In CHER-LOB, DFS was an exploratory endpoint.

PAMELA was an open-label, single-group, phase 2 trial from 22 Oct. 2013 to 30 Nov. 2015 aimed to the ability of the PAM50 HER2-enriched subtype to predict pCR at the time of surgery. Patients with HER2+ disease, stage I-IIIA and a performance status of 0-1 were given lapatinib (1,000 mg per day) and trastuzumab for 18 weeks; hormone receptor-positive patients were additionally given letrozole (2.5 mg per day) or tamoxifen (20 mg per day) according to menopausal status. Treatment after surgery was left to treating physician discretion. Median follow-up was 68.1 months (IQR 57.1-72.3). In PAMELA, DFS was an exploratory endpoint.

The Hospital Clinic and Padova University cohorts are consecutive series of patients with early-stage HER2+ breast cancer disease and a performance status of 0-1 treated, as per standard practice, from 28 Jun. 2005 to 26 Sep. 2018 (Hospital Clinic) and 23 Feb. 2009 to 26 May 2016 (Padova University cohort), with neoadjuvant trastuzumab-based multi-agent chemotherapy for 3-6 months, followed by surgery. Adjuvant treatment was completed with trastuzumab for up to 1 year, and a minimum of 5 years of hormonal therapy for patients with hormone receptor-positive tumours. Radiation therapy was administered according to local guidelines. Median follow-up of Hospital Clinic and Padova University cohorts were 39.3 (IQR 29.6-55.8) and 38.5 (IQR 30.1-65.7) months, respectively. In both cohorts, DFS was an exploratory endpoint.

The study was performed in accordance with Good Clinical Practice guidelines and the World Medical Association Declaration of Helsinki. Approvals for the study were obtained from independent ethics committees.

Example 1.2. Procedures

PAM50 and single gene analyses on formalin-fixed paraffin-embedded tumours from Short-HER, PAMELA, Padova University cohort and Hospital Clinic of Barcelona cohort were performed at IDIBAPS. Samples analysed from Short-HER were from surgical specimens, whereas samples analysed from the neoadjuvant cohorts were from baseline samples before starting neoadjuvant therapy. A minimum of −125 ng of total RNA was used to measure the expression of the 50 PAM50 subtype predictor genes, 5 genes (i.e. CD8A, PDL1, PD1, CD4 and AR) and 5 housekeeping genes. Normalization and PAM50 subtyping were performed as previously described. Regarding samples from CHER-LOB, PAM50 gene expression and subtyping was obtained from PAM50-based microarray data as previously described. Genomic analyses were performed blinded from clinical data. Nodal and tumour stages were obtained from clinical report forms. Finally, TILs were assessed on a single haematoxylin-eosin stained slide and stromal TILs were scored according to pre-defined criteria.

Example 1.3. Outcomes

The primary objective of this study was to derive and evaluate a combined prognostic score, named HER2DX, as a continuous variable. In the training dataset (i.e. Short-HER), the chosen survival endpoint was DMFS, similarly as other gene expression-based prognostic biomarkers such as the PAM50 Risk of Recurrence in hormone receptor-positive/HER2-negative breast cancer. DMFS was defined as the time between randomization and distant recurrence or death before recurrence. In the evaluation dataset, the survival endpoint was disease-free survival (DFS) due to the availability of the data, calculated as the time between treatment initiation and any of the following events, whichever first: local, regional and distant recurrence; contralateral breast cancer, excluding in situ carcinoma; other second invasive primary cancer; death before recurrence or second primary cancer. For description purposes, 5- and 8-year DMFS and DFS estimates were calculated.

The secondary objectives were: 1) to describe the clinical-pathological and genomic features of the HER2DX risk groups; 2) to explore the association of HER2DX score with DFS in the evaluation dataset according to the type of pathological response; 3) to evaluate the association of HER2DX score, and other individual variables, with pCR in the breast and axilla in the evaluation dataset. We also performed an ad-hoc analysis of the association of HER2DX with DFS in Short-HER.

Example 1.4. Statistical Analysis

The prognostic model was developed using a training dataset of 435 patients (34.7%) enrolled in the Short-HER trial. The rule to define a patient assessable in Short-HER was availability of gene expression, clinical-pathological and TILs data. Patients were split into a training set (n=290 [67.0%] of samples and 42 events [14.5%]) and a testing set (n=145 [33.0%] patients and 21 events [14.5%]), balancing for distant metastasis-free survival (DMFS) event and treatment arm. The training set was further stratified into 100 iterations of Monte-Carlo cross validation (MCCV). Cox proportional hazard models were fit to MCCV training cases using the Elastic-Net (package glmnet). A maximum of 92 features were evaluated. Elastic-Net parameters (alpha and lambda) were selected to reduce partial likelihood deviance and increase Harrell's C-index evaluated in the MCCV test sets. Selected values were then used to fit our final model against the complete training set. A total of 17 variables were selected with the following survival coefficients: nodal stage 1 (0.680), tumour stage 2-4 (0.339), MMP11 (0.200), PAM50 HER2-Enriched or Basal-like (0.156), CDC6 (0.087), CDH3 (0.076), TMEM45B (0.048), EXO1 (0.024), FGFR4 (0.021), RRM2 (0.008), TILs (−0.009), MLPH (−0.022), KRT5 (−0.024), KRT14 (−0.040), MYC (−0.050), PHGDH (−0.050) and BAG1 (−0.168).

Two cut-offs based on quartiles were defined to split patients into low- (quartile 1 and 2), medium- (quartile 3) and high-risk (quartile 4) groups. The final model was tested, as a continuous variable and using the pre-specified cut-offs, in 267 patients from the evaluation dataset. The evaluation dataset was composed of patients from CHER-LOB (n=74 [61.2%] of 121), PAMELA (n=88 [58.3%] of 151), Padova cohort (n=37) and Hospital Clinic cohort (n=68). Missing data were not included in our analyses. This study was not pre-specified in any registry.

Cox proportional hazard regression analyses were used to investigate the association of each variable with survival outcome. Genes associated with HER2DX risk groups were identified using a multi-class Significance Analysis of Microarrays and a false discovery rate <5%. Categorical variables were expressed as number (%) and compared by $\chi^2$ test or Fisher's exact test. Logistic regression analyses were performed to investigate the association of each variable with pCR. The significance level was set to a 2-sided alpha of 0.05. The software used was R code v3.6.2.

Example 1.5. Role of the Funding Source

The study was designed by investigators from Padova University and Hospital Clinic. Funding sources had no role in the design and conduct of this study, and in the analysis and interpretation of data. All authors had full access to all data and had final responsibility for the decision to submit for publication.

Example 2. Results

To build a prognostic model, clinical-pathological and molecular data were available from 435 patients of the Short-HER trial (median follow-up of 91.4 months and 63 events [14.5%]) (FIG. 1 and Table 5).

TABLE 5

Patient baseline characteristics of the Short-HER dataset.

| | All patients | | HER2DX Low | | HER2DX Med/High | | |
|---|---|---|---|---|---|---|---|
| | N | % | N | % | N | % | p-value* |
| N | 435 | — | 218 | 50.1% | 217 | 49.9% | — |
| Age (mean, range) | 55.4 (25-78) | | 55.0 (25-78) | | 55.7 (31-76) | | 0.477 |
| TILs | | | | | | | <0.001 |
| TILs 0-29 | 379 | 87.1% | 176 | 80.7% | 203 | 93.5% | |
| TILs ≥30 | 56 | 12.9% | 42 | 19.3% | 14 | 6.5% | |
| pT | | | | | | | <0.001 |
| T1 | 235 | 54.0% | 157 | 72.0% | 78 | 35.9% | |
| T2-4 | 200 | 46.0% | 61 | 28.0% | 139 | 64.1% | |
| pN | | | | | | | <0.001 |
| N0 | 264 | 60.7% | 187 | 85.8% | 77 | 35.5% | |
| N1-3 | 171 | 39.3% | 31 | 14.2% | 140 | 64.5% | |
| PIK3CA mutations | | | | | | | |
| WT | 339 | 77.9% | 169 | 77.5% | 170 | 78.3% | 1.000 |
| MUT | 92 | 21.1% | 46 | 21.1% | 46 | 21.2% | |
| NA | 4 | 1.0% | 3 | 1.4% | 1 | 0.5% | |
| Hormone receptor status | | | | | | | |
| Positive | 309 | 71.0% | 163 | 74.8% | 146 | 67.3% | 0.092 |
| Negative | 126 | 29.0% | 55 | 25.2% | 71 | 32.7% | |
| Treatmet arm | | | | | | | |
| Arm A (long) | 222 | 51.0% | 114 | 52.3% | 108 | 49.8% | 0.632 |
| Arm B (short) | 213 | 49.0% | 104 | 47.7% | 109 | 50.2% | |
| Grade | | | | | | | 0.252 |
| Grade 1 | 6 | 1.4% | 5 | 2.3% | 1 | 0.5% | |
| Grade 2 | 115 | 26.7% | 58 | 27.0% | 57 | 26.5% | |
| Grade 3 | 309 | 71.9% | 152 | 70.7% | 157 | 73.0% | |
| PAM50 | | | | | | | <0.001 |
| Luminal A | 87 | 20.0% | 63 | 28.9% | 24 | 11.1% | |
| Luminal B | 43 | 9.9% | 24 | 11.0% | 19 | 8.8% | |
| HER2-enriched | 230 | 52.9% | 75 | 34.4% | 155 | 71.4% | |
| Basal-like | 27 | 6.2% | 17 | 7.8% | 10 | 4.6% | |
| Normal-like | 48 | 11.0% | 39 | 17.9% | 9 | 4.1% | |

TILs: tumour-infiltrating lymphocytes; MUT: mutated; WT: wild-type;
*p-values represent comparison between HERDX low-risk and med/high-risk groups.

Briefly, mean age was 55.4 (25-78) and most tumours were ≤2.0 cm (54.0%), node-negative (60.7%), hormone receptor-positive (71.0%), histological grade 3 (71.9%) and had ≤10% TILs (72.6%). Concordant with previous studies[4,27], most tumours (52.9%) were PAM50 HER2-enriched (HER2-E) and the proportion of HER2-E disease was higher in hormone receptor-negative disease (69.8%) compared to hormone receptor-positive disease (46.0%). As expected, most Luminal A/B and Basal-like subtypes were hormone receptor-positive (99.2%) and hormone receptor-negative (70%), respectively.

Four variables had previously shown to provide independent prognostic information in Short-HER: 1) Tumour size, 2) Nodal status, 3) TILs and 4) PAM50 subtype. A multi-variable Cox model analysis of DMFS confirmed these findings on the 435 Short-HER patient-dataset. Next, we evaluated the ability of 31 variables to provide additional prognostic information using cross-validated (2/3 training and 1/3 testing sets) elastic net Cox models. The final score (called HER2DX) included 17 variables: tumour size (i.e. T1 vs. rest), nodal status (N0 vs. rest), TILs (as a continuous variable) and PAM50 subtype (HER2-enriched and Basal-like vs. rest), together with 13 individual genes. Among them, 7 had survival coefficients associated with poor survival outcome and were mostly tracking proliferation-related genes (i.e. CDC6, EXO1 and RRM2), HER2-enrichedrelated biology (i.e. TMEM45B and FGFR4) and Basal-like-related biology (i.e. CDH3). The other 6 genes had survival coefficients associated with better outcome and were mostly tracking Luminal A-related biology (i.e. BAG1), Normal-like (i.e. KRT5, KRT14, MLPH and MYC) and Basal-like-related biology (i.e. PHGDH). The predictive performance (C-index) of HER2DX in Short-HER was 0.80 (all patients), 0.83 (training set) and 0.72 (testing set).

HER2DX measured as a continuous variable was found significantly (p<0.001) associated with DMFS in the Short-HER 435 patient-dataset. According to HER2DX scoring based on quartiles, the 5-year DMFS of quartile 1 (Q1), Q2, Q3 and Q4 were 97.1% (95% confidence interval [CI] 94.0-100.0), 99.1% (95% CI 97.3-100.0), 88.9% (95% CI 83.2-95.0) and 73.9% (95% CI 66.0-82.7), respectively. No statistically significant difference in DMFS was observed between Q2 vs. Q1 (hazard ratio [HR]=0.92, 95% CI 0.23-3.70, p=0.910). Q3 and Q4 had significant worse DMFS compared to Q1 (Q3: HR=4.57, 95% CI 1.5-13.6, p=0.006; Q4: HR=12.0, 95% CI 4.30-33.5, p<0.001).

Figure 2:
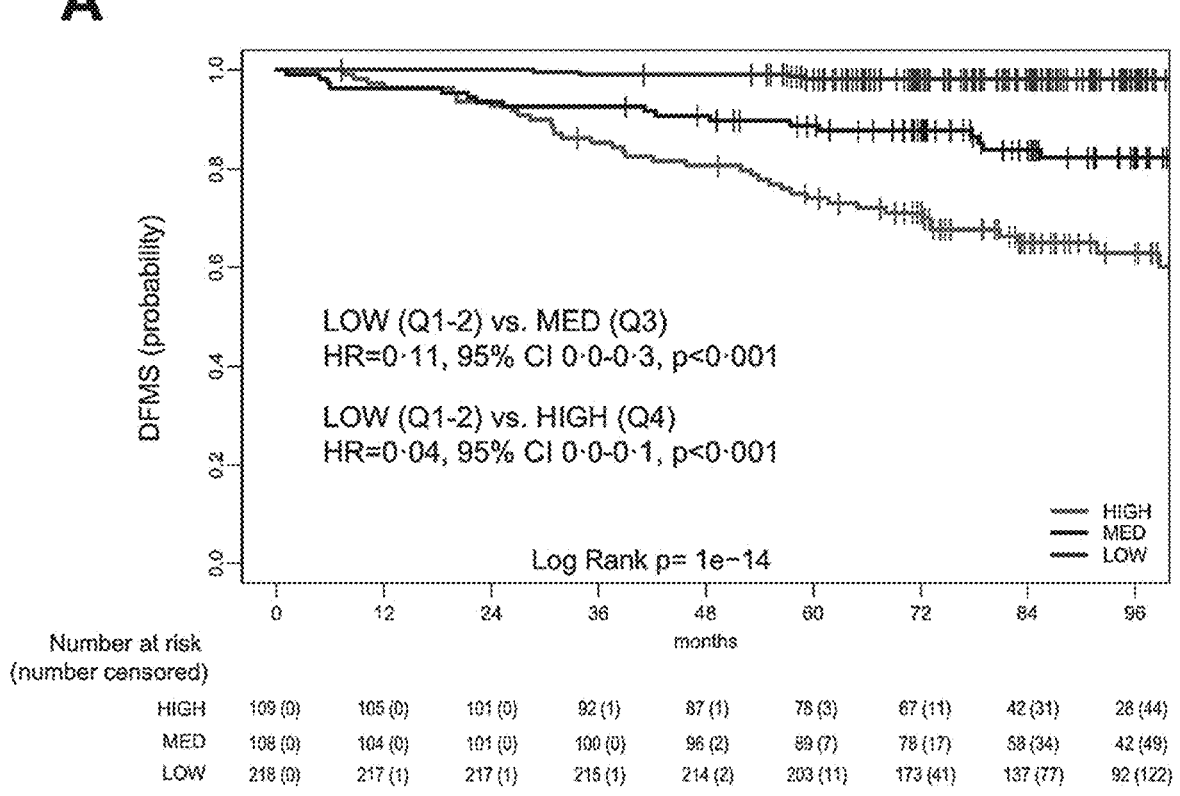
FIG. 2. Distant metastasis-free survival (DFMS) outcomes based on HER2DX score in the Short-HER training dataset. (A) DMFS according to low- (quartiles 1 and 2 combined), med-(quartile 3) and high-risk (quartile 4) scores; (B) DMFS according to low- (quartiles 1 and 2 combined) and med/high-risk (quartiles 3 and 4 combined) scores. Q, quartile.
Figure 2:
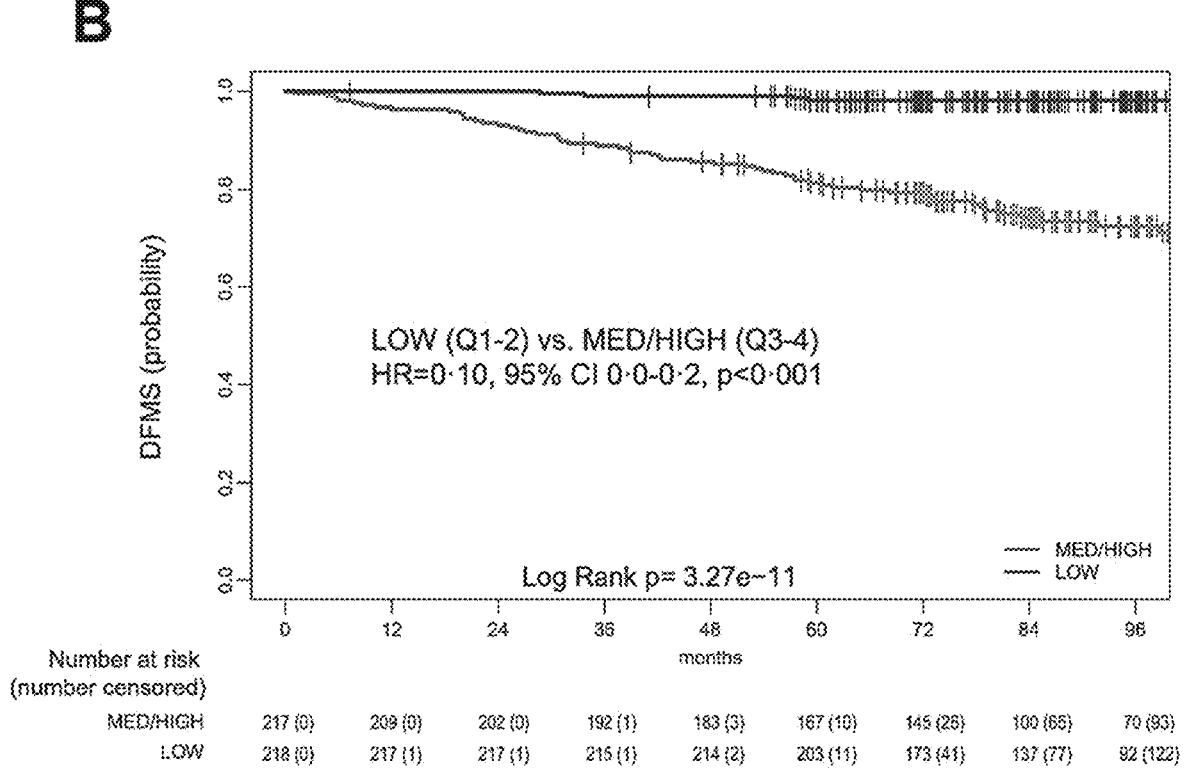

Based on these findings, HER2DX median score (i.e. Q1-2) was identified as the cut-off to identify low-risk patients (FIG. 2A). The 5-year DMFS of Q1-2 group was 98.1% (95% CI 96.3-99.9) (FIG. 2B). The HER2DX score that discriminates Q3 from Q4 was identified as the cut-off to distinguish medium- to high-risk patients. The low-risk group (Q1-2) had a significant better DMFS compared to the high-risk (Q4) group (HR=0.04, 95% CI 0.0-0.1, p<0.001) and to the medium/high-risk (Q3-Q4) group (HR=0.10, 95% CI 0.1-0.2, p<0.001). An ad-hoc analysis of HER2DX versus DFS obtained similar results.

Clinical-pathological and molecular features of the HER2DX low-risk patients in Short-HER were compared to med/high-risk patients (Table 5). No clinical-pathological or molecular feature was unique of HER2DX low-risk patients and features previously identified as being associated with poor survival outcome were also represented in the HER2DX low-risk group. In particular, in the HER2DX low-risk group, 80.7% of patients had low TILs (<30%), 28.0% had T2-4 tumours, 14.2% had N1-3 disease and 42.2% were HER2-enriched/Basal-like. Similarly, 7-36% of PGR, ESR1 and BCL2) and immune-related gene CD8A were found more expressed in HER2DX low-risk group compared to the other risk-groups. In contrast, HER2-enriched-related genes (e.g. ERBB2, GRB7 and FGFR4) and proliferation-related genes (e.g. EXO1, CCNE1 and UBE2T) were more expressed in the high-risk group compared to the other risk-groups. Of note, the medium-risk group had an intermediate gene expression profile, more like the high-risk group than the low-risk group.

A dataset of 267 patients with early-stage HER2+ breast cancer (median follow-up of 54.0 months and 30 events [11.2%]) obtained from a combined cohort of 4 neoadjuvant studies was used for an independent evaluation of the HER2DX score, which was determined at baseline before starting neoadjuvant therapy (Table 2).

TABLE 6

Patient baseline characteristics of the combined evaluation dataset.

| | All patients | | HER2DX Low | | HER2DX Med/High | | |
|---|---|---|---|---|---|---|---|
| | N | % | N | % | N | % | p-value* |
| N | 267 | — | 117 | 43.8% | 150 | 56.2% | — |
| Age (mean, range) | 54.5 (27-86) | | 53.4 (28-83) | | 55.4 (27-86) | | 0.477 |
| TILs | | | | | | | 0.009 |
| TILs 0-29 | 220 | 82.4% | 88 | 75.2% | 132 | 88.0% | |
| TILs ≥30 | 47 | 17.6% | 29 | 24.8% | 18 | 12.0% | |
| cT | | | | | | | 0.010 |
| T1 | 57 | 21.3% | 34 | 29.1% | 23 | 15.3% | |
| T2-4 | 210 | 78.7% | 83 | 70.9% | 127 | 84.7% | |
| cN | | | | | | | <0.001 |
| N0 | 148 | 55.4% | 101 | 86.3% | 47 | 31.3% | |
| N1-3 | 119 | 44.6% | 16 | 13.7% | 103 | 68.7% | |
| Pathological response | | | | | | | 0.898 |
| pCR | 98 | 36.7% | 42 | 35.9% | 56 | 37.3% | |
| Residual disease | 169 | 63.3% | 75 | 64.1% | 94 | 62.7% | |
| Hormone receptor status | | | | | | | <0.001 |
| Positive | 172 | 64.4% | 91 | 77.8% | 81 | 54.0% | |
| Negative | 95 | 35.6% | 26 | 22.2% | 69 | 46.0% | |
| Grade | | | | | | | 0.343 |
| Grade 1 | 15 | 5.9% | 5 | 4.6% | 10 | 6.8% | |
| Grade 2 | 71 | 28.0% | 35 | 32.4% | 36 | 24.7% | |
| Grade 3 | 168 | 66.1% | 68 | 63.0% | 100 | 68.5% | |
| PAM50 | | | | | | | <0.001 |
| Luminal A | 51 | 19.1% | 38 | 32.5% | 13 | 8.7% | |
| Luminal B | 33 | 12.4% | 20 | 17.1% | 13 | 8.7% | |
| HER2-enriched | 138 | 51.7% | 35 | 29.9% | 103 | 68.7% | |
| Basal-like | 21 | 7.9% | 7 | 6.0% | 14 | 9.3% | |
| Normal-like | 24 | 9.0% | 17 | 14.5% | 7 | 4.7% | |
| Study | | | | | | | 0.371 |
| PAMELA | 88 | 33.0% | 33 | 28.2% | 55 | 36.7% | |
| CHER-LOB | 74 | 27.7% | 38 | 32.5% | 36 | 24.0% | |
| HOSPITAL CLINIC | 68 | 25.5% | 30 | 25.6% | 38 | 25.3% | |
| PADOVA | 37 | 13.9% | 16 | 13.7% | 21 | 14.0% | |

TILs: tumour-infiltrating lymphocytes; pCR: pathological complete response;
*p-values represent comparison between HERDX low-risk and med/high-risk groups.

HER2DX med/high-risk patients had features previously reported to be associated with better survival outcome such as high TILs (>30%), T1 tumours or node-negative disease (Table 5).

Figure 3:
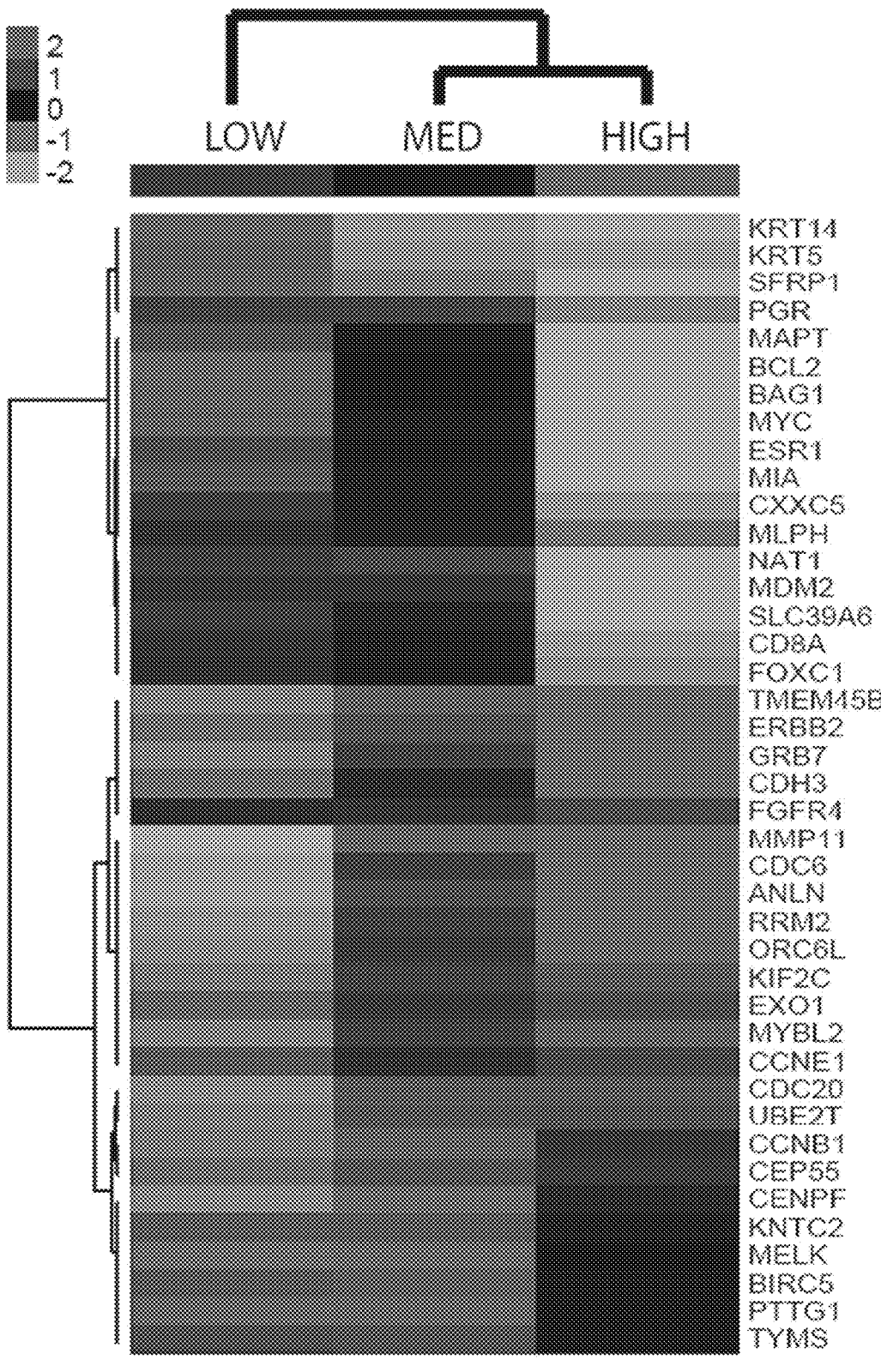
FIG. 3. Heatmap representing gene expression patterns across the three HER2DX risk groups in the Short-HER dataset. Forty-one genes found differentially expressed are shown. Red represents relative high mean expression, black median mean expression and green relative low mean expression.

Next, we explored the underlying biology of the HER2DX risk groups (low-, med- and high-). A total of 41 (75.0%) genes were found differentially expressed across the three risk groups (FIG. 3). Luminal-related genes (e.g.

All patients received chemotherapy, 1-year of trastuzumab, 43.4% (116/267) of patients received dual HER2 blockade with lapatinib and trastuzumab for 4.5 to 6.0 months and 7.5% (20/267) received 4 cycles of neoadjuvant pertuzumab. In PAMELA, chemotherapy was administered after surgery. Despite heterogeneity in systemic therapies, no statistically significant differences in DFS were observed across the 4 cohorts. In addition, pCR, which occurred in 36.7% (98/267) of cases, was associated with better DFS although it did not reach statistical significance (HR=0.43, 95% CI 0.2-1.0, p=0.063).

Figure 4:
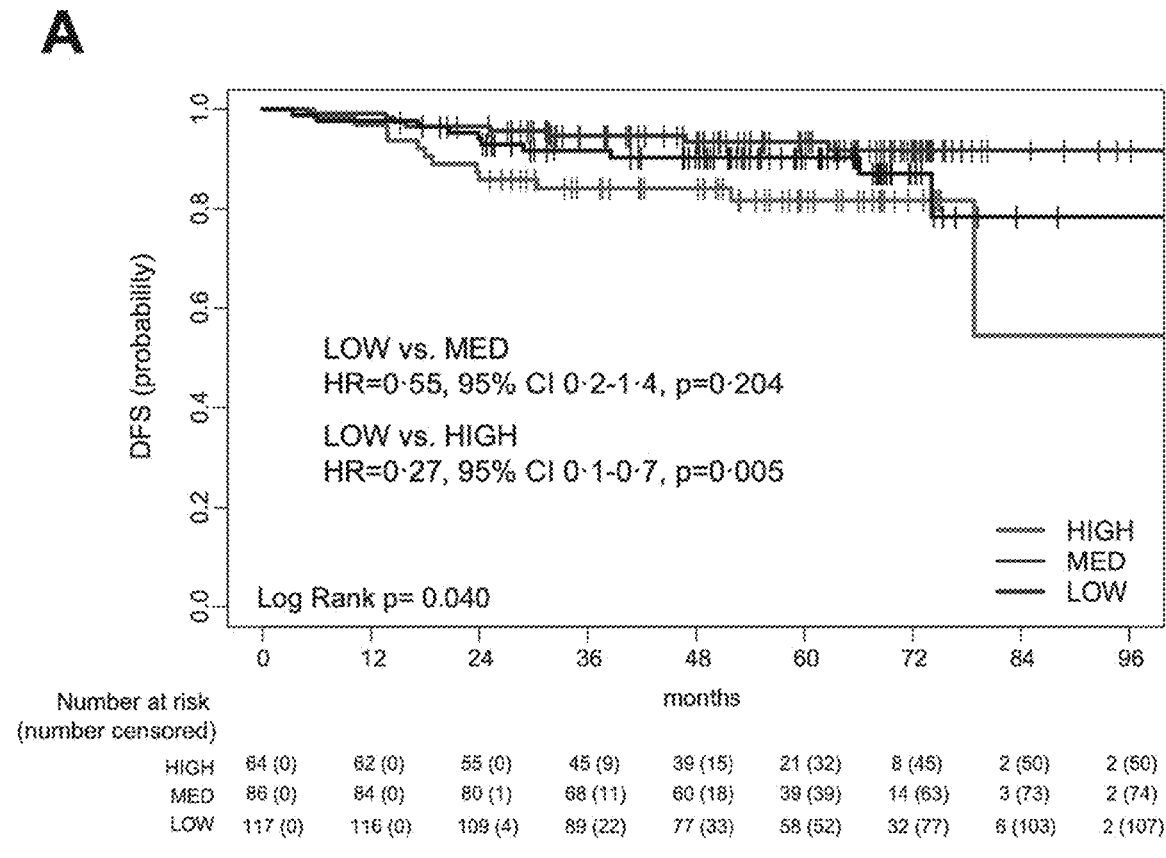
FIG. 4. Disease-free survival (DFS) outcomes based on HER2DX score in the combined evaluation dataset. (A) DFS according to low- (quartiles 1 and 2 combined), med- (quartile 3) and high-risk (quartile 4) scores; (B) DFS according to low- (quartiles 1 and 2 combined) and med/high-risk (quartiles 3 and 4 combined) scores.
Figure 4:
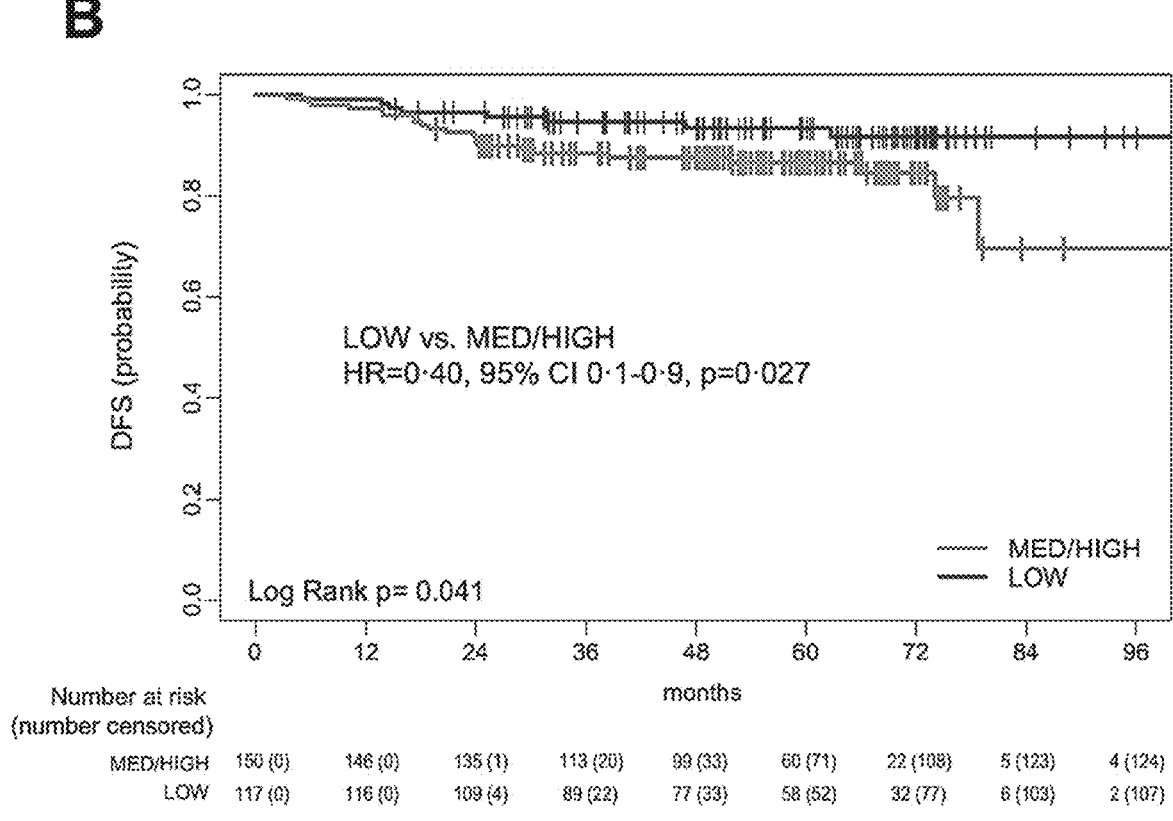

In the evaluation dataset, HER2DX score as a continuous variable was significantly associated with DFS (HR=2.77, 95% CI 1.4-5.6, p=0.004). According to the pre-specified cut-offs, HER2DX low-risk group showed a better DFS compared to the high-risk (HR=0.27, 95% CI 0.1-0.7, p=0.005) and med/high-risk (HR=0.40, 95% CI 0.1-0.9, p=0.027) groups (FIGS. 4A and B). The 5-year DFS of the HER2DX low-, high- and med/high-groups were 93.5% (95% CI 89.0-98.3%), 81.1% (95% CI 71.5-92.1%) and 86.7% (95% CI 81.2-92.5%), respectively. The 8-year DFS of the HER2DX low-, high- and med/high-groups were 91.7% (95% CI 86.2-97.6%), 54.1% (95% CI 24.1-100%) and 78.7% (95% CI 62.6-98.9%), respectively.

Concordant with previous studies, TILs as a continuous variable (odds ratio [OR]=1.04, 95% CI 1.0-1.1, p<0.0001) and HER2-E subtype (OR=3.25, 95% CI 1.8-5.7, p<0.0001) were associated with pCR. On the contrary, HER2DX score as a continuous variable was not associated with pCR (OR=1.02, 95% CI 0.6-1.6, p=0.933). According to the pre-specified cut-offs, the pCR rates in the HER2DX low-, high- and med/high-groups were 35.8% (42/117), 38.6% (34/88) and 35.5% (22/62). Among 169 patients with residual disease, the distribution of HER2DX low-, med- and high-risk groups were 44.4%, 32.0% and 23.7%, respectively. In this setting, HER2DX low-risk group showed a better DFS compared to the high-risk group (HR=0.34, 95% CI 0.1-0.9, p=0.030) but not to med-risk group (HR=0.63, 95% CI 0.2-1.7, p=0.383) and med/high-risk group (HR=0.47, 95% CI 0.2-1.1, p=0.100). The 5-year DFS of the HER2DX low- and high-groups were 90.0% (95% CI 83.2-97.4%) and 78.2% (95% CI 65.6-93.2%), respectively. The 8-year DFS of the HER2DX low- and high-groups were 87.6% (95% CI 79.7-96.3%) and 39.1% (95% CI 0.1-

100.0%), respectively. Among 98 patients who achieved a pCR, the distribution of HER2DX low-, med- and high-risk groups were 42.9%, 34.7% and 22.4%, respectively. In this setting, 0 and 6 events were observed in the low-risk and med/high-risk groups, respectively.

The invention claimed is:

1. A method of treating a patient suffering from HER2+ breast cancer comprising
   (i) measuring the level of expression of the genes [MMP11, CDC6, CDH3, TMEM45B, EXO1, FGFR4, RRM2, MLPH, KRT5, KRT14, MYC, PHGDH and BAG1] in a biological sample obtained from the patient, wherein a higher expression level of the genes [MMP11, CDC6, CDH3, TMEM45B, EXO1, FGFR4 and RRM2]; and a lower expression level of the genes [MLPH, KRT5, KRT14, MYC, PHGDH and BAG1], with respect to a pre-established reference level of expression, is indicative that the patient is a responder patient to anti-HER2 therapies, or wherein a lower expression level of the genes [MMP11, CDC6, CDH3, TMEM45B, EXO1, FGFR4, and RRM2]; and a higher expression level of the genes [MLPH, KRT5, KRT14, MYC, PHGDH, and BAG1], with respect to a pre-established reference level of expression, is indicative that the patient is a non-responder patient to anti-HER2 therapies; and
   (ii) administering anti-HER2 therapy, or a pharmaceutical composition comprising an anti-HER2 agent, optionally including pharmaceutically acceptable excipients or carriers, to the responder patient.

2. The method according to claim 1, wherein the anti-HER2 therapy is selected from: trastuzumab, pertuzumab, lapatinib, pyrotinib, poziotinib, tucatinib, neratinib, DS-8201a, SYD985 or ado-trastuzumab emtansine.

* * * * *